United States Patent
Lehrman et al.

(10) Patent No.: US 7,095,331 B2
(45) Date of Patent: Aug. 22, 2006

(54) SYSTEM AND METHOD FOR DETECTING MOTION OF A BODY

(75) Inventors: Michael L. Lehrman, Washington, DC (US); Michael D. Halleck, Northglenn, CO (US); Edward L. Massman, Dallas, TX (US)

(73) Assignee: iLife Solutions, Inc., Dallas, TX (US)

( * ) Notice: Subject to any disclaimer, the term of this patent is extended or adjusted under 35 U.S.C. 154(b) by 0 days.

(21) Appl. No.: 10/796,595

(22) Filed: Mar. 9, 2004

(65) Prior Publication Data

US 2005/0110648 A1 May 26, 2005

Related U.S. Application Data

(63) Continuation of application No. 09/909,404, filed on Jul. 19, 2001, now Pat. No. 6,703,939, which is a continuation-in-part of application No. 09/396,991, filed on Sep. 15, 1999, now Pat. No. 6,307,481.

(60) Provisional application No. 60/265,521, filed on Jan. 31, 2001.

(51) Int. Cl.
*G08B 21/00* (2006.01)

(52) U.S. Cl. ............. 340/669; 340/539.1; 340/573; 340/426; 464/566; 464/559; 464/578

(58) Field of Classification Search ............. 340/573.1, 340/669, 539.12, 426, 539.1, 573; 464/566, 464/578, 559

See application file for complete search history.

(56) References Cited

U.S. PATENT DOCUMENTS

| | | | | |
|---|---|---|---|---|
| 5,694,340 A | * | 12/1997 | Kim ........................... | 702/141 |
| 5,879,309 A | * | 3/1999 | Johnson et al. ............. | 600/552 |
| 5,941,836 A | * | 8/1999 | Friedman .................... | 600/595 |
| 5,953,683 A | * | 9/1999 | Hansen et al. ................ | 702/95 |

* cited by examiner

*Primary Examiner*—Tai T. Nguyen

(57) ABSTRACT

The present invention comprises a system and method for detecting an acceleration of a body and for evaluating movement of a body relative to an environment to detect falls and irregular motions of the body. According to an exemplary embodiment, the system comprises a sensor and a controller that comprises a processor. The sensor, which is associable with the body, comprises a plurality of acceleration measuring devices and is capable of repeatedly sensing accelerative phenomena of the body. The controller, which is associated with the sensor, is operable to process the sensed accelerative phenomena as a function of at least one accelerative event characteristic. The controller determines when the body experiences an acceleration that represents a particular type of motion. The controller also determines when a static acceleration vector reaches a value indicative of a fall. After a fall has occurred, the controller is capable of determining whether the controller was connected to a body during the fall or whether only the controller experienced the fall.

20 Claims, 13 Drawing Sheets

X FILTER

Y FILTER

X FILTER

Y FILTER

SYSTEM AND METHOD FOR DETECTING MOTION OF A BODY

RELATED APPLICATIONS

This application is a continuation of prior U.S. application Ser. No. 09/909,404 filed on Jul. 19, 2001, now U.S. Pat. No. 6,703,939.

This patent application is a continuation in part of U.S. patent application Ser. No. 09/396,991 filed Sep. 15, 1999 now U.S. Pat. No. 6,307,481 by Lehrman et al. entitled "Systems For Evaluating Movement of A Body and Methods of Operating The Same." This patent application is also related to U.S. Provisional Patent Application No. 60/265,521 filed Jan. 31, 2001 by Lehrman et al. entitled "System and Method for Detecting an Acceleration of a Body." U.S. patent application Ser. No. 09/396,991 and U.S. Provisional Patent Application No. 60/265,521 are both assigned to the assignee of the present invention. The disclosures in U.S. patent application Ser. No. 09/396,991 and in U.S. Provisional Patent Application No. 60/265,521 are hereby incorporated by reference in the present application as if fully set forth herein.

TECHNICAL FIELD OF THE INVENTION

The present invention relates generally to means for detecting motions of a body, and, more particularly, relates to systems and methods of operation thereof, for evaluating movement of a body relative to an environment to identify occurrences of irregular body motions or falls.

BACKGROUND OF THE INVENTION

Methods for determining specific movements of a body that use a variety of devices, apparatus and systems are, generally speaking, known. The term "body" is defined broadly hereafter and includes both organic and inorganic objects.

In point of fact, many methods are known for sensing body movement, or non-movement (i.e., sensed dynamic accelerations, including cessation of movement), as well as, for sensing body movement over time, which is commonly used to determine comparative levels of activity of a monitored body (See, U.S. Pat. Nos. 4,110,741, 4,292,630, 5,045,839, and 5,523,742). These methodologies, however, merely report various levels of body activity, and, simply stated, fail to recognize possible causes for any increased or decreased level of body activity.

In contrast, other methodologies have developed over time for the detection of falls (See also, U.S. Pat. Nos. 4,829,285, 5,477,211, 5,554,975, and 5,751,214). These methodologies are largely based upon the utilization of one or more mechanical switches (e.g., mercury switches) that determine when a body has attained a horizontal position. These methods however fail to discern "normal," or acceptable, changes in levels of body activity. Stated another way, the foregoing fall detection methodologies provide no position change analysis and, therefore, cannot determine whether a change in position, once attained, is acceptable or unacceptable.

Various training methods have been conceived for sensing relative tilt of a body (See, U.S. Pat. Nos. 5,300,921 and 5,430,435), and some such methodologies have employed two-axis accelerometers. The output of these devices, however, have reported only static acceleration of the body (i.e., the position of a body relative to earth within broad limits). It should be appreciated that static acceleration, or gravity, is not the same as a lack of dynamic acceleration (i.e., vibration, body movement, and the like), but is instead a gauge of position. While accelerometers that measure both static and dynamic acceleration are known, their primary use has heretofore been substantially confined to applications directed to measuring one or the other, but not both.

Thus, it may be seen that the various conventional detectors fall into one of two varieties, those that gauge movement of the body and those that gauge a body's position by various means, with neither type capable of evaluating body movement to determine whether the same is normal or abnormal; and if abnormal, whether such movement is so abnormal to be beyond tolerance, for instance, to be damaging, destructive, crippling, harmful, injurious, or otherwise alarming or, possibly, distressing to the body. None of the methodologies heretofore known have provided a suitable means to evaluate body movement over time and to determine whether such movement is tolerable. Further improvement could thus be utilized.

SUMMARY OF THE INVENTION

To address the above-introduced deficiencies of the prior art, the present invention introduces systems, as well as methods of operating such systems, for evaluating movement of a body relative to an environment. For the purposes hereof, the term "body" is defined broadly, meaning any organic or inorganic object whose movement or position may suitably be evaluated relative to its environment in accordance with the principles hereof; and where the term "environment" is defined broadly as the conditions and the influences that determine the behavior of the physical system in which the body is located.

An advantageous embodiment of a system that evaluates movement of a body relative to an environment in accordance herewith includes both a sensor and a processor. In operation, the sensor is associated with the body and operates to repeatedly sense accelerative phenomena of the body. The processor, which is associated with the sensor, processes the sensed accelerative phenomena as a function of at least one accelerative event characteristic to determine whether the evaluated body movement is within environmental tolerance. The processor also preferably generates state indicia while processing the sensed accelerative phenomena, which represents the state of the body within the environment over time.

For the purposes hereof, the term "sensor" is defined broadly, meaning a device that senses one or more absolute values, changes in value, or some combination of the same, of at least the sensed accelerative phenomena. According to an advantageous embodiment, described in detail hereafter, the sensor may be a plural-axis sensor that senses accelerative phenomena and generates an output signal to the processor indicative of measurements of both dynamic and static acceleration of the body in plural axes.

According to this embodiment, the processor receives and processes the output signal. The processor is preferably programmed to distinguish between normal and abnormal accelerative events, and, when an abnormal event is identified, to indicate whether the abnormal event is tolerable, or within tolerance. In further embodiments, the processor may be programmed to distinguish other physical characteristics, including temperature, pressure, force, sound, light, relative position, and the like.

It should be noted that the relevant environment may be statically or dynamically represented. The sophistication of any such representation may be as complex or as uncomplicated as needed by a given application (e.g., disability, injury, infirmity, relative position, or other organic assistance monitoring; cargo or other transport monitoring; military, paramilitary, or other tactical maneuver monitoring; etc.). It should further be noted that any representation may initially be set to, or reset to, a default, including, for instance, a physically empty space, or vacuum.

Regardless, the principles of the advantageous exemplary embodiment discussed heretofore require at least one accelerative event characteristic to be represented to enable the processor to determine whether the evaluated body movement is within environmental tolerance, which is again advantageously based upon both dynamic and static acceleration measurements.

According to a related embodiment, the processor is further operable, in response to processing the sensed accelerative phenomena, to generate state indicia, which includes tolerance indicia, generated in response to determining whether the evaluated body movement is within environmental tolerance. Preferably, such tolerance indicia is compared with at least one threshold, likely associated with the accelerative event characteristic. In response to such comparison, the processor controls a suitable indicating means to initiate an alarm event; to communicate such tolerance indicia to a monitoring controller; to generate statistics; or the like.

According to a related advantageous embodiment, the system may be associated with other components or sensing systems. For instance, in an assistance monitoring application, the sensor may repeatedly sense dynamic and static acceleration of the body in the plural axes and generate output signals indicative of the measurements. The processor continuously processes the output signals to distinguish between selected accelerative and non-selected accelerative events (described in detail hereafter) based upon both the dynamic and the static acceleration of the body, and generates state indicia, including tolerance indicia, that is communicated to a remote monitoring controller. The tolerance indicia is communicated to the monitoring controller for record keeping/statistical purposes, as well as to provide "live" monitoring of the individual subscriber.

Communication between the processor and the controller may be by a wireless network, a wired network, or some suitable combination of the same, and may include the Internet. Preferably, the system generates an alert whenever the monitored subscriber is in "jeopardy," as determined by the system, such as in response to a debilitating fall by the subscriber. In a further embodiment, the processor is operable to repeatedly generate "heartbeat" indicia that indicates that the system is in an operable state, whereby absence of the same informs the monitoring controller that some other part of the system is malfunctioning.

The foregoing has outlined rather broadly the features and technical advantages of the present invention so that those skilled in the art may better understand the DETAILED DESCRIPTION OF THE INVENTION that follows. Additional features and advantages of the invention will be described hereinafter that form the subject of the claims of the invention. Those skilled in the art should appreciate that they may readily use the conception and specific embodiments disclosed as a basis for modifying or designing other structures for carrying out the same purposes of the present invention. Those skilled in the art should also realize that such equivalent constructions do not depart from the spirit and scope of the invention in its broadest form.

Before undertaking the DETAILED DESCRIPTION OF THE INVENTION, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, and the term "associable" may mean to include, be included within, interconnect with, contain, be contained within, connect to or with, couple to or with, be communicable with, cooperate with, interleave, juxtapose, be proximate to, be bound to or with, have, have a property of, or the like; and the terms "controller" and "processor" mean any device, system or part thereof that controls at least one operation, such a device may be implemented in hardware, firmware or software, or some suitable combination of at least two of the same. It should be noted that the functionality associated with any particular controller/processor may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DESCRIPTION OF THE INVENTION

FIGS. 1 through 14, discussed below, and the various embodiments used to describe the principles of the present invention in this patent document are by way of illustration only and should not be construed in any way to limit the scope of the invention. Those skilled in the art will understand that the principles of the present invention may be implemented in any suitably arranged system for detecting the motion of a body.

Figure 1:
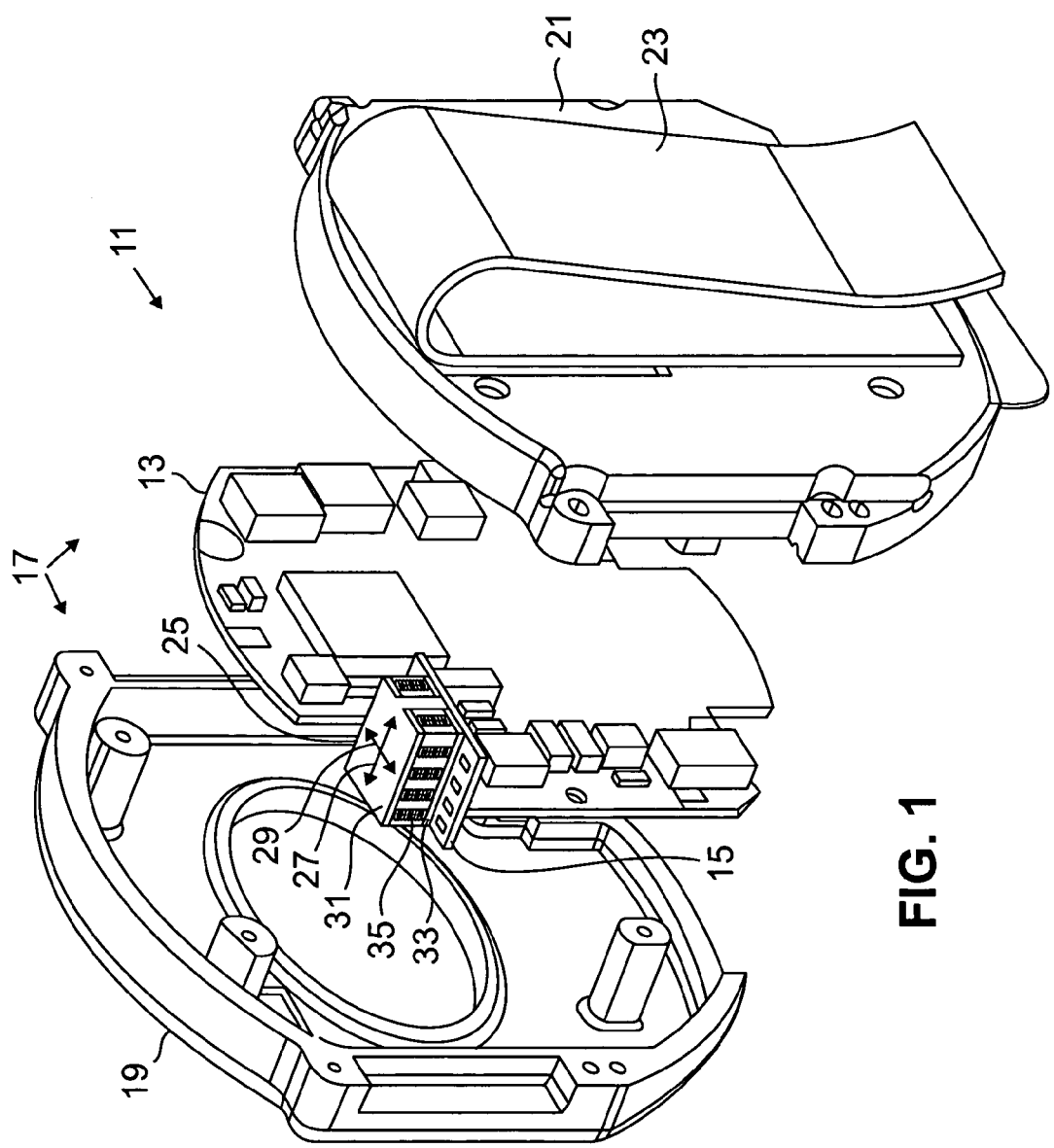
FIG. 1 illustrates an isometric view of an exemplary embodiment of a system that evaluates body movement in accordance with the principles of the present invention.

FIG. 1 illustrates an isometric view of an exemplary embodiment of a system (generally designated 11) that evaluates body movement in accordance with the principles of the present invention, and more particularly that measures and distinguishes selected accelerative events of a body (not shown). As used in this disclosure, the phrases "accelerative events" or "accelerative phenomena" are defined as occurrences of change in velocity of the body (or acceleration), whether in magnitude, direction or both.

System 11 includes circuit boards 13 and 15 (connected boards at right angles to one another) that are associated with a housing (generally designated 17) utilizing known mounting techniques. Exemplary housing 17 (and system 11, for that matter), when assembled, is approximately one centimeter thick and is approximately five centimeters across in any direction.

Housing 17 may comprise, for example, exemplary housing halves 19 and 21 that encase boards 13 and 15, although those skilled in the art will understand that any configuration suitable for a particular implementation of the invention may be arranged.

Exemplary rear half 21 is provided with a clip 23 for associating system 11 with the body (e.g., people, animals, objects of various sorts, etc.). Exemplary clip 23 is shown as a mechanical spring-type clip, but could be any known attachment device or system, including either mechanical or chemical attachment systems, or any other suitable means for associating system 11 with the body.

System 11 includes a processor (shown in FIG. 2) and a sensor 25. Exemplary sensor 25 operates to sense accelerative phenomena of the body, and is mounted on circuit board 13 with x and y axes, 27 and 29, respectively, oriented thereat (though other orientations could be utilized).

Sensor 25 is illustratively shown as a plural-axis (dual shown) acceleration measuring device suitably mounted on a single monolithic integrated circuit (one conventional sensor is an accelerometer available from ANALOG DEVICES, INC., located at One Technology Way, Norwood, Mass., United States of America, namely, Model No. ADXL202). Sensor 25 includes polysilicon surface-micromachined sensor layer 31 built on top of silicon wafer 33. Polysilicon springs 35 resiliently suspend sensor layer 31 over the surface of wafer 33 providing resistance against acceleration forces. Deflection of the sensor layer is measured using a differential capacitor formed by independent fixed and central plates, the fixed plates driven by one hundred eighty degrees (180°) out of phase square waves having amplitude proportional to acceleration. Signal outputs from each axis of sensor 25 are conditioned (i.e., phase sensitive demodulation and low pass filtering) and presented at analog output nodes. While not utilized in the primary advantageous embodiment of this invention, the ANALOG DEVICES' accelerometer is operable to convert the analog signals to duty cycle modulated ("DCM") signals at a DCM stage providing digital output signals capable of being directly counted at a processor.

While techniques for reconstructing analog signals from the digital output signals may suitably be utilized (e.g., passing the duty cycle signals though an RC filter), thereby allowing use of the digital signal output of a sensor of system 11 hereof, use of the analog signal outputs has been found advantageous due to the increased bandwidth availability (0.01 Hz to 5 kHz, adjustable at capacitors at the output nodes to bandlimit the nodes implementing low-pass filtering for antialiasing and noise reduction), and the measuring sensitivity that may be attained. A typical noise floor of five hundred micro "g" per Hertz ($500 \times 10^{-6}$ "g"/Hz) is achieved, thereby allowing signals below five milli "g" ($5 \times 10^{-3}$ "g") to be resolved for bandwidths below 60 Hz. The value "g" is the acceleration of gravity at the surface of the earth (32 feet/sec$^2$ or 9.8 m/sec$^2$)

According to the illustrated embodiment, sensor 25 generates analog output voltage signals corresponding to measurements in the x and y axes, which include both an alternating current (ac) voltage component proportional to G forces (i.e., dynamic acceleration component related to vibrations of sensor layer 31) and a direct current (dc) voltage component proportional to an angle relative to earth (i.e., static acceleration component related to gravity). This open loop acceleration measurement architecture, capable of measuring both static and dynamic acceleration, can thus be utilized to determine position of a body by measuring both the x and y output voltages simultaneously, as well as measure forces of impact experienced by a body. This information comprises state indicia, and utilizing both signal components from both outputs, the sensed accelerative phenomena of the body may subsequently be processed to distinguish a variety of accelerative phenomena and, ultimately, to selectively act based on the distinctions, as is described in detail hereafter to determine whether the evaluated body movement is normal or abnormal, and, if abnormal, whether the same is within tolerance.

It is noted that the foregoing embodiment has been introduced for illustrative purposes only. In alternate embodiments, any sensor that is capable of sensing accelerative phenomena relative to a body may be used in lieu of, or even in conjunction with, sensor 25. Further, alternate orientations of sensor 25 may be used for different applications.

Figure 2:
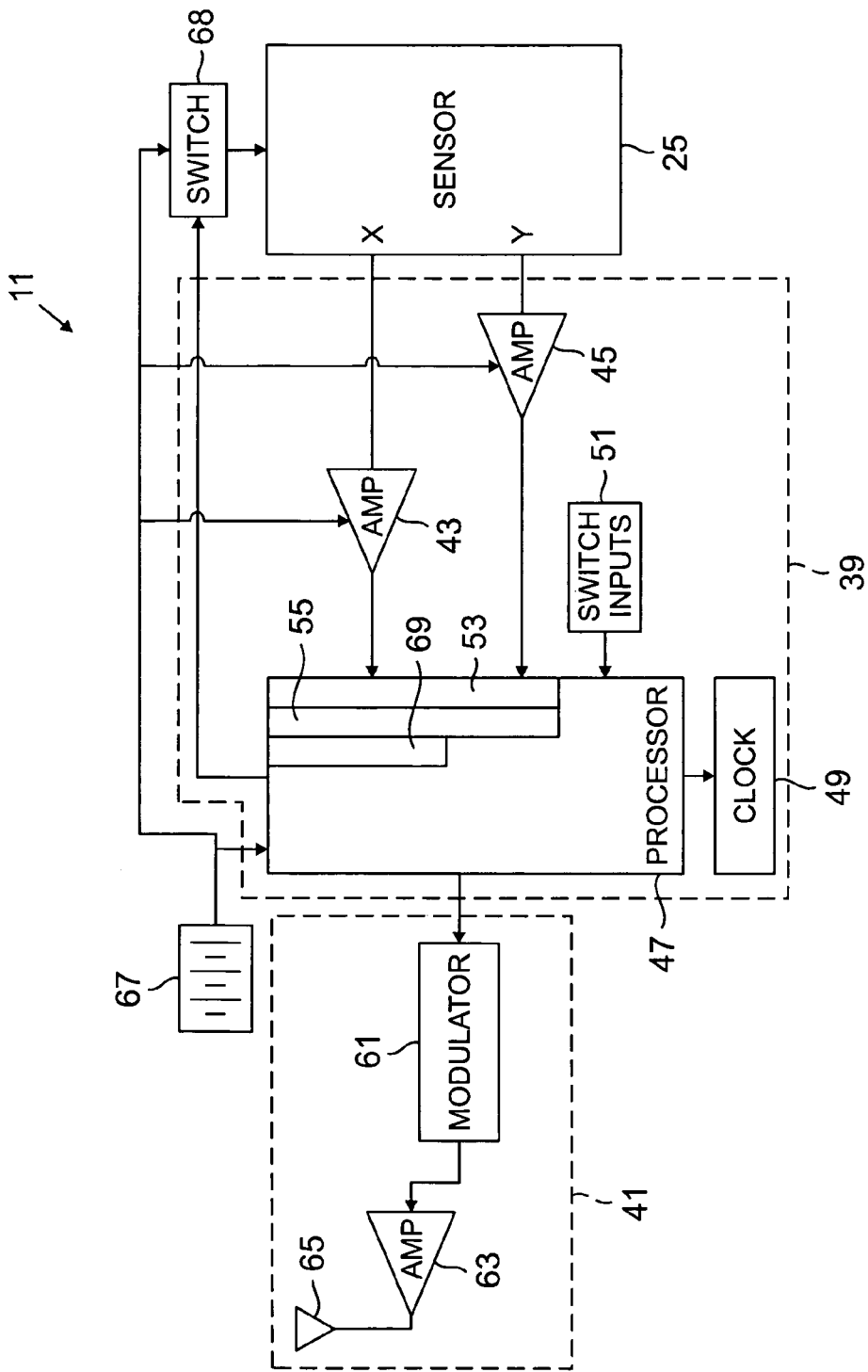
FIG. 2 illustrates a block diagram of the exemplary system set forth with respect to FIG. 1.

Turning next to FIG. 2, there is illustrated a block diagram of the exemplary system of FIG. 1, which includes processing circuitry 39, indicating means 41, power supply 67, and switch 68, along with sensor 25.

Exemplary processing circuitry 39 illustratively includes a processor 47 and buffer amplifiers 43 and 45 that buffer the analog x and y outputs from sensor 25. Exemplary processor 47, which is associated with sensor 25, is capable of processing the sensed accelerative phenomena as a function of at least one accelerative event characteristic to thereby determine whether an evaluated body movement is within environmental tolerance. Processor 47 also preferably generates state indicia while processing the sensed accelerative phenomena, which may represent the state of the body within the environment over time. Processor 47 is associated with a crystal oscillator/clock 49, switch (DIP) inputs 51, an analog-digital conversion circuitry 53 and a DSP filter 55 (one conventional processor is available from TEXAS INSTRUMENTS, INC., located in Dallas, Tex., United States of America, namely, Model No. MSP430P325).

Exemplary indicating means 41, in response to direction from processor 47, is operable to accomplish at least one of the following: initiate an alarm event; communicate such state, or tolerance, indicia to a monitoring controller; generate statistics; etc. Indicating means 41 may take any number of forms, however, for use in system 11 of the present embodiment, stage 41 is an RF transmitter including RF modulator 61 enabled by processor 47. Exemplary data is presented and modulated at modulator 61, amplified at amplifier 63 and transmitted at antenna 65 (to a remote receiver unit as discussed hereinafter).

According to the present embodiment, power for the various components of system 11 is provided by power supply 67, which illustratively is a 3.6 volt lithium ion battery. Low power management may suitably be under the control of processor 47 utilizing exemplary switched/power supply voltage FET switch 68 at sensor 25, which provides power only during sampling cycles, and operates to shut components down during non-use cycles. For instance, processor 47 may be taken off-line when processing is complete, reducing current drain.

It should be noted that the various circuitry discussed heretofore has been introduced herein for illustrative purposes only. System 11 may be implemented using any suitably arranged computer or other processing system including micro, personal, mini, mainframe or super computers, as well as network combinations of two or more of the same. In point of fact, in one advantageous embodiment, sensor 25 and processor 47 are not co-located, but rather associated wirelessly. To that end, the principles of the present invention may be implemented in any appropriately arranged device having processing circuitry. Processing circuitry may include one or more conventional processors, programmable logic devices, such as programmable array logic ("PALs") and programmable logic arrays ("PLAs"), digital signal processors ("DSPs"), field programmable gate arrays ("FPGAs"), application specific integrated circuits ("ASICs"), large scale integrated circuits ("ILSIs"), very large scale integrated circuits ("VLSIs") or the like, to form the various types of circuitry, processors, controllers or systems described and claimed herein.

Conventional computer system architecture is more fully discussed in THE INDISPENSABLE PC HARDWARE BOOK, by Hans-Peter Messmer, Addison Wesley (2nd ed. 1995) and COMPUTER ORGANIZATION AND ARCHITECTURE, by William Stallings, MacMillan Publishing Co. (3rd ed. 1993); conventional computer, or communications, network design is more fully discussed in DATA NETWORK DESIGN, by Darren L. Spohn, McGraw-Hill, Inc. (1993); conventional data communications is more fully discussed in VOICE AND DATA COMMUNICATIONS HANDBOOK, by Bud Bates and Donald Gregory, McGraw-Hill, Inc. (1996), DATA COMMUNICATIONS PRINCIPLES, by R. D. Gitlin, J. F. Hayes and S. B. Weinstein, Plenum Press (1992) and THE IRWIN HANDBOOK OF TELECOMMUNICATIONS, by James Harry Green, Irwin Professional Publishing (2nd ed. 1992); and conventional circuit design is more fully discussed in THE ART OF ELECTRONICS, by Paul Horowitz and Winfield Hill, Cambridge University Press (2nd ed. 1991). Each of the foregoing publications is incorporated herein by reference for all purposes.

Figure 3A:
FIGS. 3A to 3D illustrate exemplary strip chart records of output of the sensor introduced in FIGS. 1 and 2 taken during illustrative situations.
Figure 3B:
Figure 3C:
Figure 3D:
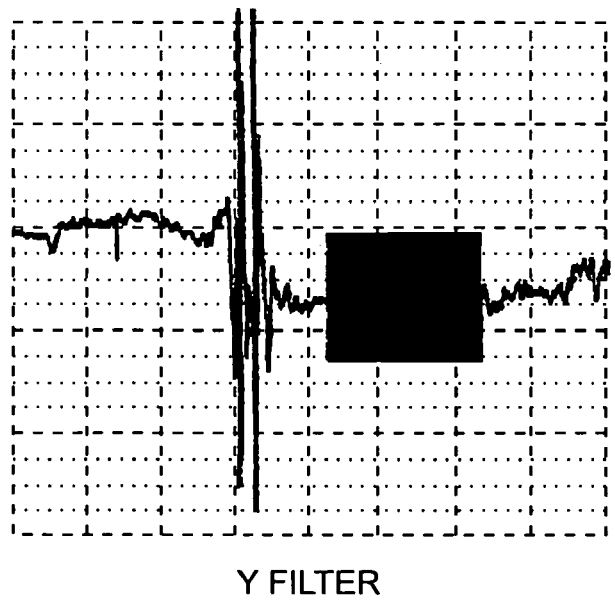

Turning next to FIGS. 3A to 3D, illustrated are exemplary strip chart records of output of exemplary sensor 25 of FIGS. 1 and 2 taken during illustrative situations. More particularly, FIGS. 3A and 3B illustrate the analog signal at the x and y outputs of sensor 25 during a fall by a body to the left, and whereas FIGS. 3C and 3D illustrate the analog signal at the x and y outputs of sensor 25 during a fall by a body to the right (the dark blocks indicating an alarm condition). As can be seen from the exemplary traces, a fall to the left and to the right are both distinguishable by the disruption of a stable position, or normal body movement, by a concussive force followed by a distinctly different ending stable position. According to the illustrative embodiment introduced herein, the direction of fall is clear from the position of the ending trace at the y outputs. If the fall had been more forward or backward, the x output traces would likewise clearly indicate the same (this assumes x and y sensor axes orientation as set forth in FIG. 1). Of course, the same x and y outputs of the sensor 25 may be suitably processed to simply determine position of the body, for instance, such as when a person-is lying down, when a box has tipped over, etc.

Figure 4:
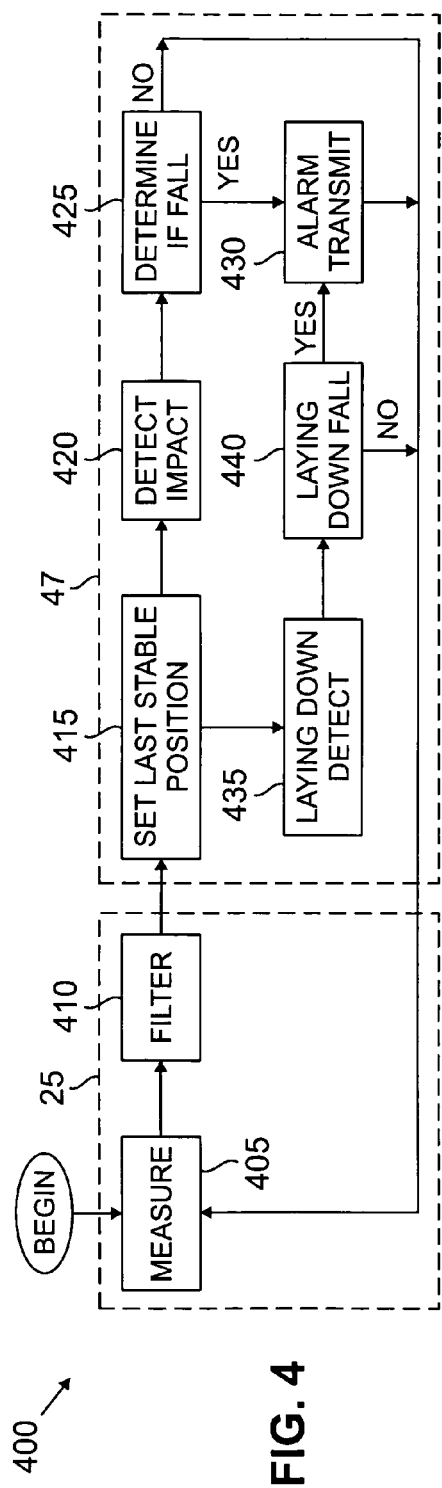
FIG. 4 illustrates an operational flow diagram of an exemplary method of programming a processor in accordance with a fall detection application of the principles of the present invention.

Turning next to FIG. 4, illustrated is operational flow diagram of an exemplary method (generally designated 400) of programming of processor 47 in accordance with a fall detection application of the principles of the present invention. For the purposes of illustration, concurrent reference is made to system 11 of FIGS. 1 and 2. It should be noted that this illustration introduces an exemplary operational method for programming processor 47 for its use as a fall detector, and that suitable alternate embodiments of system 11 for evaluating movement of a body relative to different environments may likewise be implemented in accordance with the principles hereof, such as for relative position, other assistance monitoring, transparent monitoring, tactical maneuver monitoring, etc.

Exemplary method 400 begins and a request for sampling measurements is generated, likely by processor 47 (Step 405), either in response to an executing operations program or upon initiation by a user, possibly remotely from a monitoring controller (discussed with reference to FIG. 8). Sensor 25 senses x and y acceleration values generating measurement signals at the outputs at sensor 25.

In the present implementation, the measurement signals are converted from analog to digital format and filtered by filter 55 (Step 410; thereby reducing probability that an out-of-tolerance abnormal movement will be determined incorrectly in response to a single sharp impact, such as a collision between mount 17 and a hard surface when sensor 25 is off the body causing a sharp signal spike).

Processor 47 uses direct current (dc) voltage components of the outputs from sensor 25 to determine a last stable position of the body on which sensor 25 is mounted (Step 415). More particularly, processor 47 repeatedly compares successive input values with immediately preceding input values and, if within tolerance, are added thereto and stored in an accumulator. This is repeated until Z samples have been accumulated and added over some defined period of time (e.g., one second) or until a received input is out of tolerance, in which case the sampling cycle is reinitiated. When Z samples are accumulated and added, the accumulated value is divided by Z to determine a "last stable" static acceleration average value, which is saved and is indicative of the last stable position of the body. Sampling and/or sampling cycle rates may be varied, but, while preferably not continuous due to power consumption concerns, should be substantially continual. It is important to note, therefore, that such characteristics may be statically maintained or dynamically generated.

Processor 47 uses alternating current (ac) voltage components of each output from sensor 25 to check against a G force threshold value set at DIP switch 51 to see if it exceeds the threshold (Step 420—thus qualifying as a potential fall impact, in the current example, possibly an intensity in excess of about 2 to 4 G depending upon desired sensitivity). According to the present implementation, if three of these dynamic acceleration measurements are received in excess of the threshold without five intervening measurements that are less than the threshold, the impact detect flag may be set.

Processor 47 determines a fall by testing a post-impact stream of samples against a tolerance (Step 425; for instance, a selected value of the ac voltage components, for example a value less than about 2 G). Each new sample is tested against the previous sample to see if the position of the body has stabilized. When the position has stabilized to less than the tolerance, W samples are averaged to get the new stable static acceleration average value corresponding to the new stable position.

Processor 47, in response to the value corresponding to the new stable position is shifted indicating a change of body position of 45° or more from the last stable position, classifies the event as a debilitating fall and alert stage 41 is activated (Step 430). A greater stabilization or post-stabilization sample period may be selected to allow more time for an uninjured user to rise without issuance of an alert.

Processor 47, after setting the last stable position, adds the absolute values of the x and y last stable positions together, and, then determines whether the body associated with sensor 25 is lying down if the added value exceeds a value corresponding to 90° plus or minus twenty five percent (25%) (Step 435). In such case, after a selected time (for example, four seconds) with repeated like values, the laying down detect flag is set. While this flag is set, any impact that exceeds the G force threshold is treated as a debilitating fall (Step 440). The flag is set only as long as the added value continues to indicate that the wearer is lying down.

It should be noted that the foregoing embodiment was introduced for illustrative purposes only and that the present invention broadly introduces systems, as well as methods of operating such systems, that evaluate movement of a body relative to an environment, which in the above-given example is an assistance monitoring environment. An important aspect of the present invention is that processor 47 is operable to process sensed accelerative phenomena as a function of at least one accelerative event characteristic, and that such characteristics will largely be defined by the specific application. Therefore, system 11, and, more particularly, processor 47, generates state indicia relative the environment of interest, and determines whether the evaluated body movement is within tolerance in the context of that environment. For instance, "tolerance" would likely be very different for a monitored body of an elderly person with a heart condition, a toddler, a box in a freight car, a container of combustible gas, etc.

Figure 5:
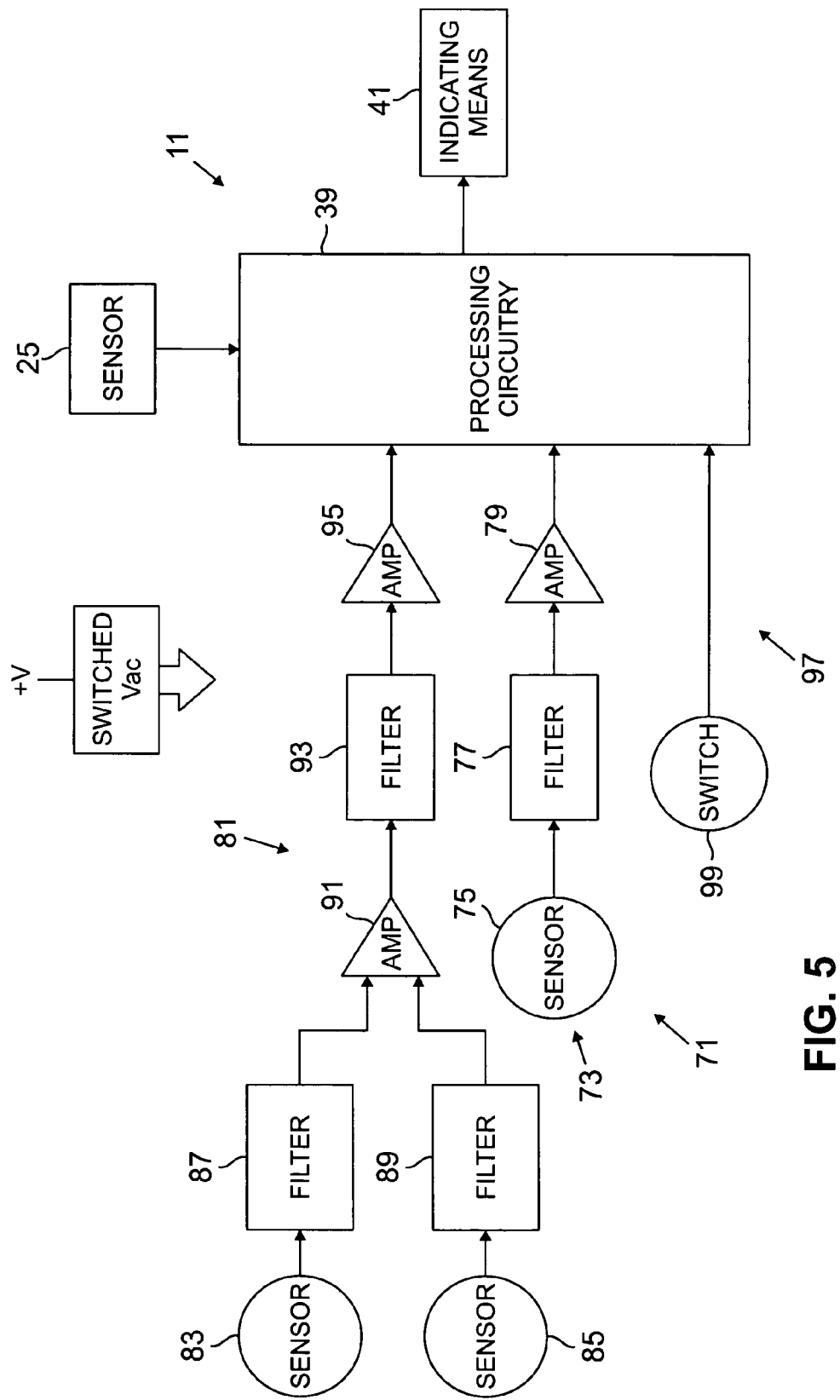
FIG. 5 illustrates a functional block diagram of an alternate sensing system that may suitably be associated with the processor of the present invention.

Turning next to FIG. 5, illustrated is a functional block diagram of an alternate sensing system (generally designated 71) that may suitably be associated with processor 47 of FIGS. 1, 2, and 4 in accordance with the principles of the present invention. In this embodiment, components utilizable with system 11 are configured again as a human fall monitor/detector, and any or all of these additional monitoring functions may be employed with system 11. For purposes of illustration, concurrent reference is made to processor 47 of FIGS. 2 and 4.

Exemplary sensor 71 includes a respiration module 73, which includes a body contact breath sensor 75 (for example a volumetric sensor, or a near body breath sensor), low pass filter 77 and amplifier 79 providing output signals indicative of respiration rate and vitality to processor 47. The outputs are processed and, when a dangerous respiratory condition is suggested (generates state indicia relative the environment, and determines whether the evaluated body movement (broadly defined herein to include organic physiologic phenomena) is within environmental tolerance), an identifiable (for example, by signal coding) alarm is sent indicating means 41.

Sensor 71 further includes an ECG module 81, which includes input electrodes 83 and 85 providing heart rate signals to filters 87 and 89. The filtered signals are amplified at amplifier 91 and band pass filtered at filter 93. The output is amplified at 95 for input to processor 47 and processed so that dangerous heart rhythms and events can be detected (generates state indicia relative the environment, and determines whether the evaluated body movement is within environmental tolerance) and an identifiable alarm sent at alert stage 41.

Sensor 71 further includes a panic button module 97 that is operable using a standard user activated switch 99 positioned at housing 17 allowing a user to initiate a call for help. The switch output is input to processor 47 to initiate an identifiable alarm at alert stage 41.

Figure 6:
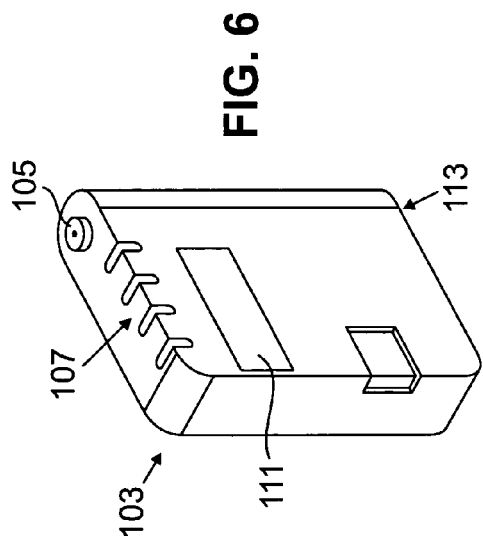
FIG. 6 illustrates a perspective view of an exemplary remote receiver unit of the system of this invention.
Figure 7:
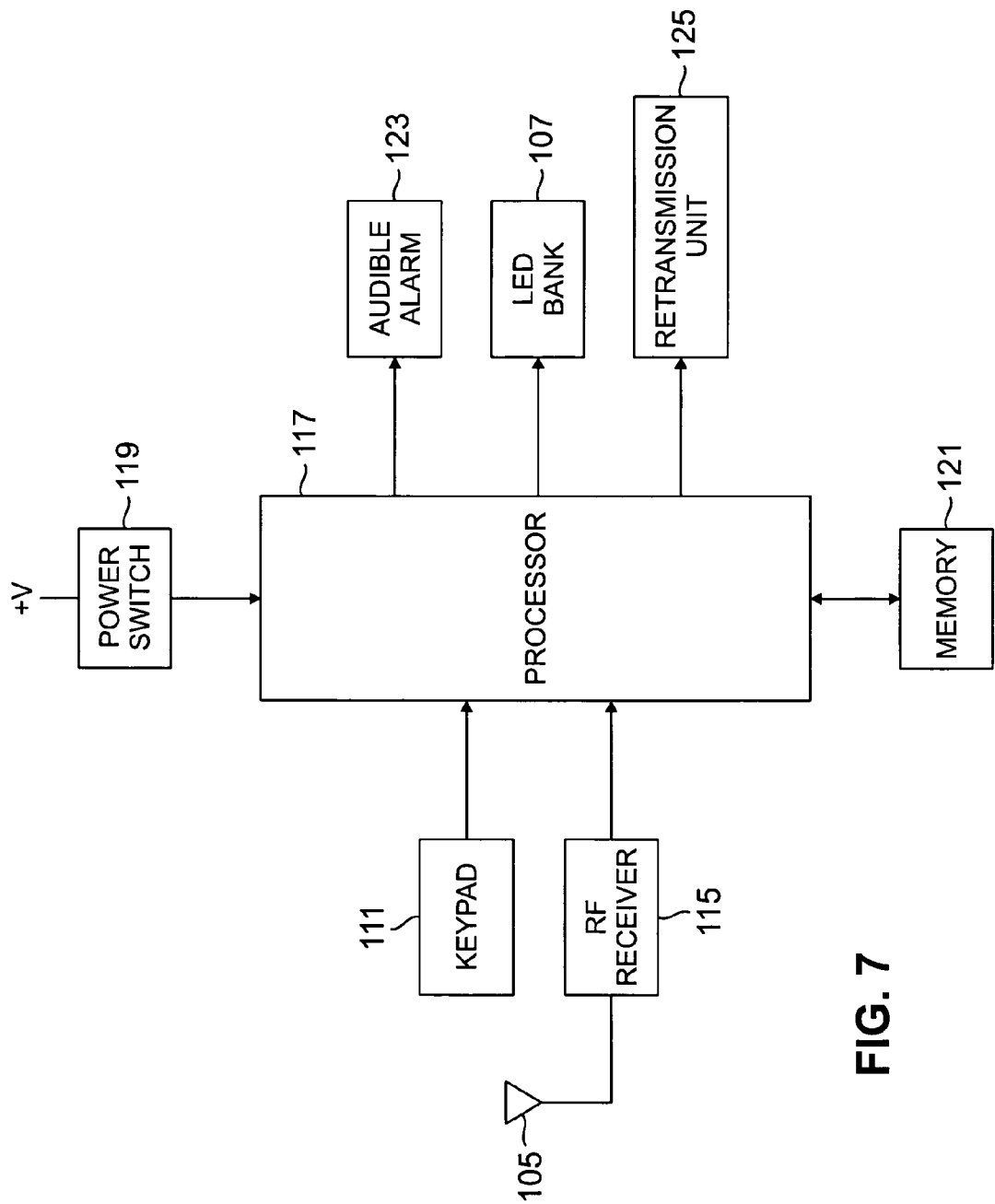
FIG. 7 illustrates a functional block diagram of the exemplary receiver unit of FIG. 6.

Turning momentarily to FIGS. 6 and 7, illustrated are a perspective view of an exemplary remote receiver unit of the system of this invention and a functional block diagram of the same. In a distributed system in accord with one embodiment of this invention, a remote receiver unit 103 (for example a wall mountable unit) as shown in FIGS. 6 and 7 is provided for receipt of transmissions from sensor 25 and/or system 71. Unit 103 includes a receiver antenna 105, indicator LEDs 107 (including indicators for as many detector functions as are employed in the specific embodiment of the apparatus being monitored, as well as an indicator for unit on/off status), and a user interface input keypad 111 for unit setup, reset and alarm deactivation. Power access 113 is provided at the bottom of the unit.

RF receiver 115 is tuned to receive alarm transmissions from sensor 71 and presents the signal received for processing at processor 117 for alarm identification and appropriate output. Processor 117 also receives inputs from keypad 111 and power switch 119. Non-volatile memory 121 is provided for input of identification of the user and/or of the apparatus being monitored. Audible alarm 123, LED bank 107 and retransmission unit 125 (an autodialer, imbedded digital cellular technology, RF transmitter, an Internet appliance, or the like) are connected to receive outputs from processor 117.

When a transmission is received, or when battery power at the body mounted apparatus is low, an audible alarm is sounded and the appropriate LED (indicative of the condition causing the alarm, for example a debilitating fall by a user of apparatus 11) is activated. If not disabled by the user at key pad 111 within a short period, processor 117 activates retransmission unit 125 initiating a call for help or other remote notification.

Operational setup of unit 103 is also accomplished under programming at processor 117 and by sequential operation by a user or technician of keypad 111 and/or power switch 119 as is known (including user ID set, learn mode operations, reset or reprogramming operations, and urgency code operations).

Figure 8:
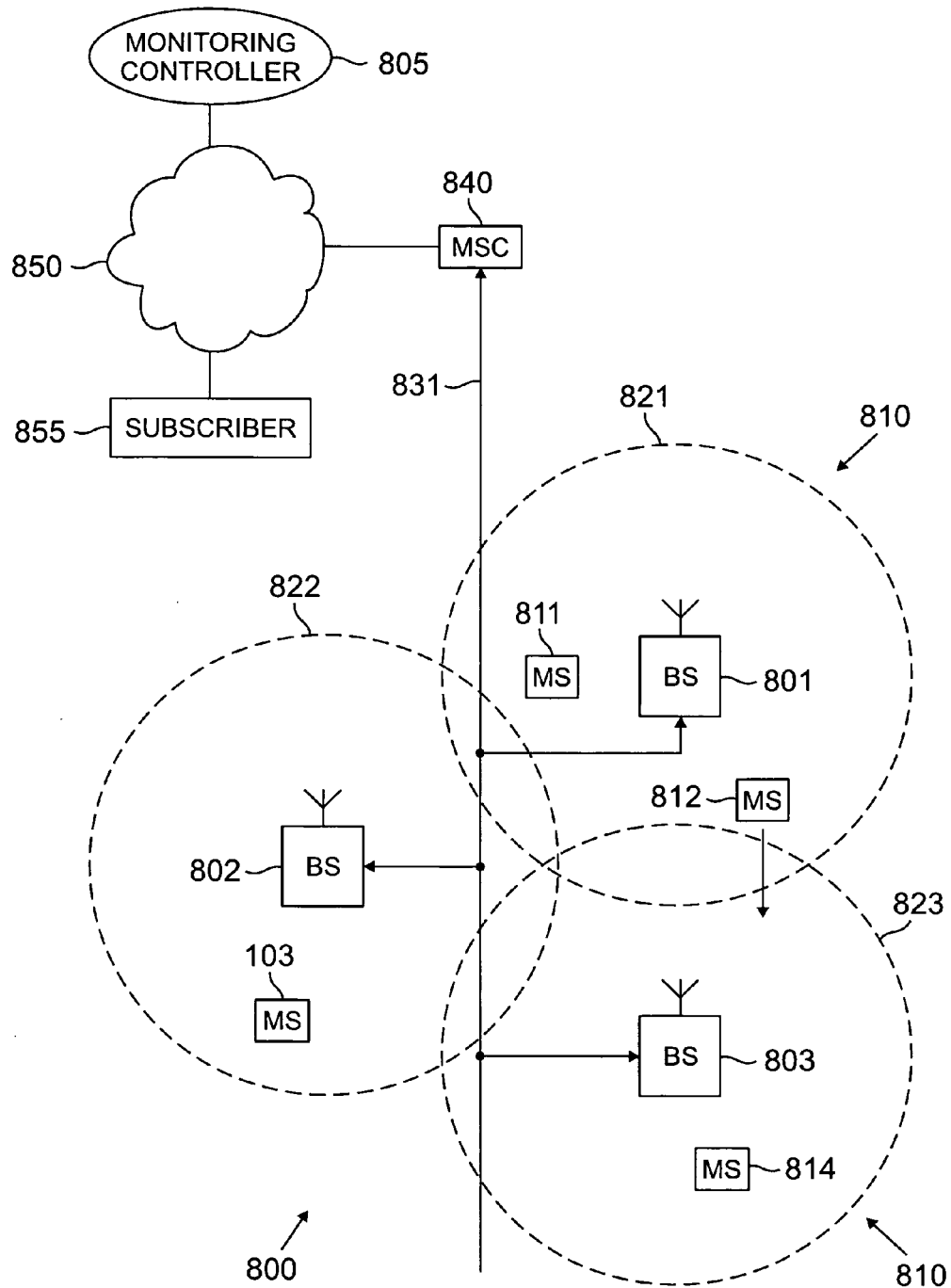
FIG. 8 illustrates an exemplary wireless network that is associated via a wired network, such as the Internet, to a remote monitoring controller according to one embodiment of the present invention.

Turning next to FIG. 8, illustrated is an exemplary hybrid wireless/wired network (generally designated 800) that is associated with a remote monitoring controller 805 according to one embodiment of the present invention. The wireless network 810 is introduced for illustrative purposes only, and comprises a plurality of cell sites 821 to 823, each containing one of the base stations, BS 801, BS 802, or BS 803. Base stations 801 to 803 are operable to communicate with a plurality of mobile stations (MS) including MS 103 (remote receiver unit 103), and MS 811, MS 812 and MS 814. Mobile stations MS 103, and MS 811, MS 812 and MS 814, may be any suitable cellular devices, including conventional cellular telephones, PCS handset devices, portable computers, metering devices, transceivers, and the like (including, for instance, remote receiver unit 103).

Dotted lines show the approximate boundaries of the cell sites 821 to 823 in which base stations 801 to 803 are located. The cell sites are shown approximately circular for the purposes of illustration and explanation only. It should be clearly understood that the, cell sites also may have irregular shapes, depending on the cell configuration selected and natural and man-made obstructions.

In one embodiment of the present invention, BS 801, BS 802, and BS 803 may comprise a base station controller (BSC) and a base transceiver station (BTS). Base station controllers and base transceiver stations are well known to those skilled in the art. A base station controller is a device that manages wireless communications resources, including the base transceiver station, for specified cells within a wireless communications network. A base transceiver station comprises the RF transceivers, antennas, and other electrical equipment located in each cell site. This equipment may include air conditioning units, heating units, electrical supplies, telephone line interfaces, and RF transmitters and RF receivers, as well as call processing circuitry. For the purpose of simplicity and clarity in explaining the operation of the present invention, the base transceiver station in each of cells 821, 822, and 823 and the base station controller associated with each base transceiver station are collectively represented by BS 801, BS 802 and BS 803, respectively.

BS 801, BS 802 and BS 803 transfer voice and data signals between each other and the public telephone system (not shown) via communications line 831 and mobile switching center (MSC) 840. Mobile switching center 840 is well known to those skilled in the art. Mobile switching center 840 is a switching device that provides services and coordination between the subscribers in a wireless network and external networks 850, such as the Internet, public telephone system, etc. Communications line 831 may be any suitable connection means, including a T1 line, a T3 line, a fiber optic link, a network backbone connection, and the like. In some embodiments of the present invention, communications line 831 may be several different data links, where each data link couples one of BS 801, BS 802, or BS 803 to MSC 840.

In the exemplary wireless network 800, MS 811 is located in cell site 821 and is in communication with BS 801, MS 103 is located in cell site 822 and is in communication with BS 802, and MS 814 is located in cell site 823 and is in communication with BS 803. MS 812 is also located in cell site 821, close to the edge of cell site 823. The direction arrow proximate MS 812 indicates the movement of MS 812 towards cell site 823.

For the purposes of illustration, it is assumed that system 11 is associated with an elderly person whose residence is wirelessly monitored. It is further assumed that sensor 25 is associated with the elderly person and that processor 47 is coupled in MS/remote receiver unit 103, such that sensor 25 and processor 47 are wirelessly associated.

System 11 repeatedly senses various physiological phenomena of the elderly person, including accelerative phenomena of his body. Remote processor 47 processes the repeatedly sensed phenomena, and, particularly, the accelerative phenomena of the body, as a function of at least one accelerative event characteristic to thereby determine whether the evaluated body movement is within environmental tolerance. Processor 47 advantageously generates state indicia while processing the sensed accelerative phenomena, representing the state of the body within the environment over time.

Exemplary processor 47 is programmed to distinguish between normal and abnormal accelerative events (e.g., walking, sitting, lying down, etc. versus tripping, falling down, etc.), and, when an abnormal event is identified, indicates whether the abnormal event is tolerable, or within tolerance. Processor 47 may also suitably be programmed to distinguish other physical characteristics, including temperature, pressure, force, sound, light, relative position (including lying down), and the like.

As processor 47 generates state indicia, which includes tolerance indicia, it uses the same to determine whether the evaluated body movement is within environmental tolerance. Preferably, such tolerance indicia is compared with at least one threshold, likely associated with the accelerative event characteristic. In response to such comparison, processor 47 controls a suitable indicating means to initiate an alarm event (locally and via network 810 to monitoring controller 805), to communicate such tolerance indicia to a monitoring controller 805, to generate statistics (locally and via network 810 to monitoring controller 805), or the like.

According to a related advantageous embodiment, such state indicia, and other information is communicated from time to time to monitoring controller 805, from which such information may suitably be perceived. For instance, a technician, medical professional, or relative might wish to review the activities and status of the elderly person. This may easily be facilitated via a centralized data repository accessible via the Internet, or via any other suitably arranged network. While viewing such information, the technician, medical professional, or relative (subscriber 2, generally designated 855) might initiate a diagnostic equipment check, a physiological test, a simple status check, or the like. Similarly, monitoring controller 805, via the network 800, may monitor a "heartbeat" signal generated periodically by MS/remote receiver unit 103, the heartbeat indicating that unit 103 is functional.

Figure 9:
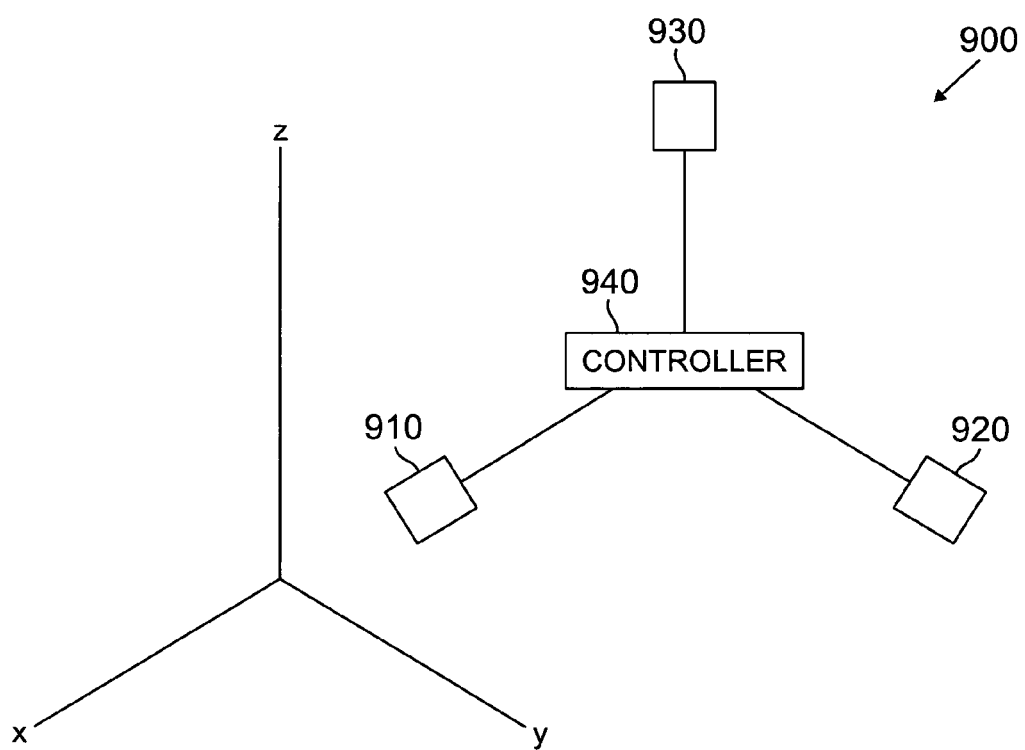
FIG. 9 illustrates an exemplary embodiment of the system of the present invention for evaluating body movement with a plurality of acceleration measuring devices.

FIG. 9 is a schematic drawing of an alternate advantageous embodiment 900 of the present invention. As shown in FIG. 9 sensor 25 of embodiment 900 comprises three acceleration measuring devices 910, 920 and 930. The number three is illustrative only. It is clear that sensor 25 comprises a plurality of acceleration measuring devices and is not limited to a particular number of acceleration measuring devices.

Acceleration measuring devices 910, 920 and 930 may each comprises a plural axis measuring device of the type previously described. For convenience, the acceleration measuring devices will be referred to as accelerometers.

Accelerometers 910, 920 and 930 are each connected to controller 940. Controller 940 comprises processing circuitry 39 (including processor 47), indicating means 41, power supply 67 and switch 68, of the types previously described.

As shown in FIG. 9, accelerometer 910, accelerometer 920, and accelerometer 930 are each coupled directly to controller 940. As an electrical circuit connection, it is said that accelerometer 910 and accelerometer 920 are connected to controller 940 in an electrically parallel connection. The connections of accelerometer 910 and accelerometer 920 to controller 940 are not geometrically parallel to each other. In at least one advantageous embodiment of the present invention the connections of accelerometer 910 and accelerometer 920 to controller 940 are located at right angles with respect to each other. The combination of accelerometer 920 and accelerometer 930 and the combination of accelerometer 910 and accelerometer 930 are similarly arranged.

In one arrangement of this advantageous embodiment of the present invention, accelerometer 910 is aligned parallel to the x-axis of a three dimensional Cartesian coordinated system and is capable of measuring accelerations in the x direction. Accelerometer 920 is aligned parallel to the y-axis and is capable of measuring accelerations in the y direction. Accelerometer 930 is aligned parallel to the z-axis and is capable of measuring acceleration in the z direction.

Controller 940 is capable of simultaneously determining the values of acceleration measured by each of accelerometers 910, 920 and 930. In this manner, controller 940 can determine the values of acceleration in x, y and z directions. Processor 47 in controller 940 is capable of adding the values of acceleration in the x, y and z directions to obtain a vector sum (i.e., magnitude and direction) of the body (not shown) to which accelerometers 910, 920 and 930 are attached. It is noted that although embodiment 900 has been described for use with a three dimensional Cartesian coordinate system, other three dimensional coordinate systems may also be used.

Figure 10:
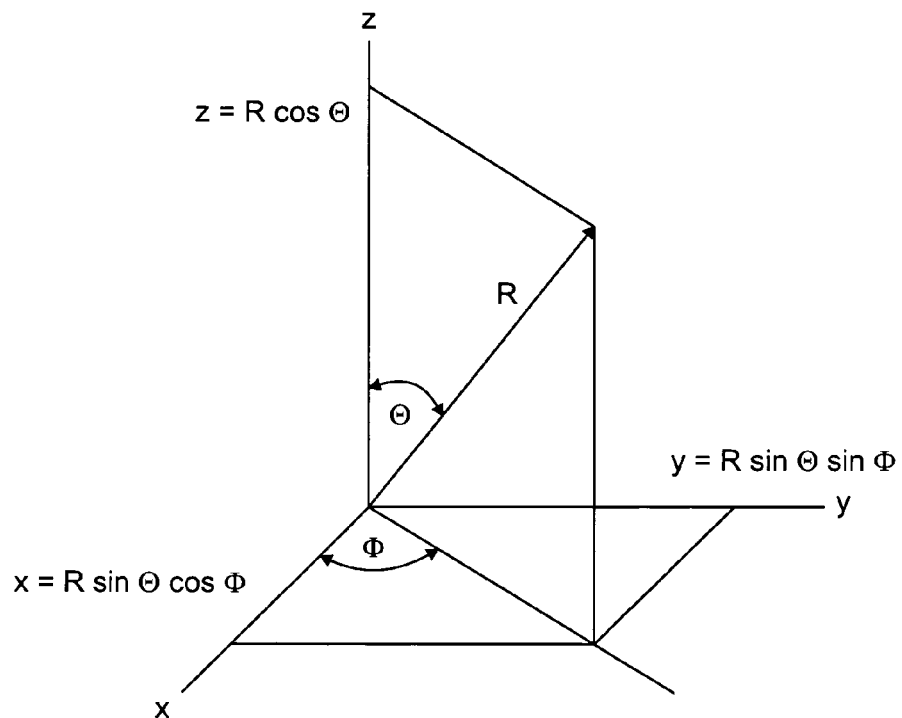
FIG. 10 illustrates the coordinate relationships between a three dimensional Cartesian coordinate system and a three dimensional spherical polar coordinate system.

For example, FIG. 10 illustrates a three dimensional spherical polar coordinate system having coordinates R, $\Theta$, $\Phi$. FIG. 10 also illustrates the relationships between a Cartesian coordinate system superimposed on the spherical polar coordinate system. The coordinate R is radial coordinate. The magnitude of R equals the distance from the origin of the coordinate system to the end of a vector that originates at the origin. The coordinate $\Theta$ is an angular coordinate that measures the angle between the vector and the z axis. The coordinate $\Theta$ is measured in the plane formed by the vector and the z axis. The coordinate $\Phi$ is an angular coordinate that measures the angle between the x axis and the projection of the vector on the x-y plane. The coordinate $\Phi$ is measured in the x-y plane.

As is shown in FIG. 10, the relationships between the Cartesian coordinates and the spherical polar coordinates are given by:

$$x = R \sin \Theta \cos \Phi \quad (1)$$

$$y = R \sin \Theta \sin \Phi \quad (2)$$

$$z = R \cos \Phi \quad (3)$$

The values of R, $\Theta$, $\Phi$ may be calculated from the values x, y, z by the formulas:

$$R = [x^2 + y^2 + z^2]^{1/2} \quad (4)$$

$$\Theta = \tan^{-1}[[x^2 + y^2]^{1/2}/z] \quad (5)$$

$$\Phi = \tan^{-1}[y/x] \quad (6)$$

As previously mentioned, a plurality of accelerometers may be used. Although each accelerometer 910, 920 and 930 is shown in FIG. 9 as a single accelerometer, this arrangement is illustrative only. Each accelerometer 920, 920 and 930 may be replaced with two or more accelerometers (not shown). In other words, additional accelerometers (now shown) may be used in addition to accelerometers 910, 920 and 930 shown in FIG. 9. The additional accelerometers may be oriented in any chosen direction and are not limited to being in the same plane as one of the accelerometers 910, 920 and 930 (or in the same plane as one of the additional accelerometers). In general, accelerometers comprising sensor 25 may be coupled in series, in parallel, or in a combination of series and parallel connections.

Accelerometer 910 is capable of generating analog output voltage signals corresponding to measurements of acceleration in the x direction. Similarly, accelerometer 920 is capable of generating analog output voltage signals corresponding to measurements of acceleration in the y direction and accelerometer 930 is capable of generating analog output voltage signals corresponding to measurements of acceleration in the z direction.

The analog output voltage signals of accelerometer 910, 920 and 930 each comprise both an alternating current (ac) voltage component proportional to G forces (i.e., dynamic acceleration component related to vibrations of sensor layer 31 of sensor 25) and a direct current (dc) voltage component proportional to an angle relative to earth (i.e., static acceleration component related to gravity "g").

The direct current (dc) voltage components from accelerometers 910, 920 and 930 (representing static acceleration due to gravity in their respective x, y and z directions) may be combined to obtain a value of the acceleration that the body experiences due to gravity. In general, the vector R represents the resultant of combining the x, y and z components of acceleration experienced by the body. When a body is at rest (i.e., dynamic acceleration is zero), the vector R represents the static acceleration due to gravity.

Because the value of gravity at the earth's surface is substantially constant for any point on the surface of the earth, the value of gravitational acceleration (obtained by vectorially summing the gravitational acceleration components) will be the same for each measurement. That is, the vector sum of each set of gravitational acceleration components will always give the same total value of gravitational acceleration experienced by the body as long as the body is at rest relative to an inertial frame of reference. This value is the gravitational acceleration of approximately thirty two feet per second per second (32 ft/sec$^2$) or approximately nine and eight tenths meters per second per second (9.8 m/sec$^2$). This value is customarily referred to as one "g."

Processor 47 in controller 940 is capable of being programmed to sound an alarm condition when controller 940 receives signals from accelerometers 910, 920 and 930 that exceed an alarm limit set in accordance with pre-programmed instructions. In this manner, controller 940 can identify when the body to which accelerometers 910, 920 and 930 have been coupled has experienced an acceleration that exceeds a specified value.

Processor 47 is capable of combining the alternating current (ac) voltage components from accelerometers 910, 920 and 930 (representing dynamic acceleration due to external forces in their respective x, y and z directions) and the direct current (dc) voltage components from accelerometers 910, 920 and 930 (representing static acceleration due to gravity in their respective x, y and z directions) to obtain a total value of the acceleration that the body experiences (due to dynamic acceleration and due to gravity). Because the value of acceleration due to gravity will always be equal to one "g", any total value of acceleration that exceeds one "g" will be caused by the presence of dynamic acceleration on the body.

In an advantageous embodiment of the present invention, processor 47 is programmed to sound an alarm condition when controller 940 receives signals from accelerometers 910, 920 and 930 that indicate that the total value of acceleration detected exceeds one "g." In this manner, controller 940 determines that the body has experienced dynamic acceleration due to external forces because the measured acceleration has exceeded the "background" acceleration reading that is always present from gravitational acceleration.

Controller 940 receives the total acceleration signal in the x direction from accelerometer 910, and the total acceleration signal in the y direction from accelerometer 920, and the total acceleration signal in the z direction from accelerometer 930. Controller 940 then combines the total acceleration components to obtain the total acceleration experienced by the body. Controller 940 then subtracts the value of one "g" from the total acceleration. If the result is greater than zero, then controller 940 has determined that the body has experienced dynamic acceleration due to external forces. Controller 940 then sends an alarm signal in the manner previously described.

Figure 11:
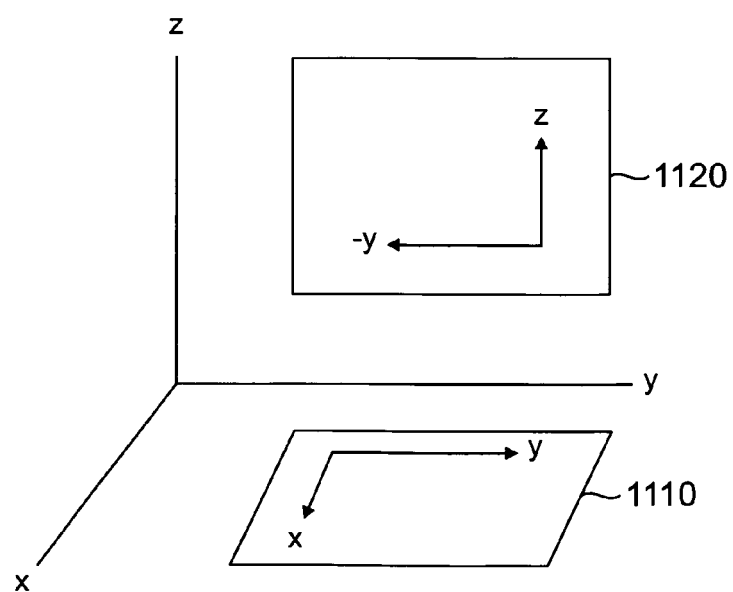
FIG. 11 illustrates the orientation of a first plural axis accelerometer in an x-y plane of a three dimensional Cartesian coordinate system and the orientation of a second plural axis accelerometer in a y-z plane of the same Cartesian coordinate system.

In an alternate advantageous embodiment of the present invention, a first plural axis accelerometer 910 and a second plural axis accelerometer 920 are coupled to controller 940 in the orientations shown in FIG. 11. Accelerometer 910 is aligned as shown in frame 1110. The first axis of accelerometer 910 is aligned parallel to the x axis and the second axis of accelerometer is aligned parallel to the y axis. Accelerometer 920 is aligned as shown in frame 1120. The first axis of accelerometer 920 is aligned parallel to the negative y axis and the second axis of accelerometer 920 is aligned parallel to the z axis.

An advantage is to be gained by aligning accelerometer 910 and accelerometer 920 in this manner. When accelerometer 910 and accelerometer 920 share a common axis it is possible to scale out any inconsistencies between the readings of the two accelerometers. For example, assume that it is known that a force exists in the y direction. Then the force in the y direction will be the same for both of the two accelerometers. Assume that accelerometer 910 gives a reading of "1.0" for the y direction force and that accelerometer 920 gives a reading of "0.9" for the y direction force. If it is determined that accelerometer 910 has the correct reading, then accelerometer 920 can be "scaled up" (i.e., corrected) to compensate for inconsistencies in the manufacture of accelerometer 920.

Figure 12:
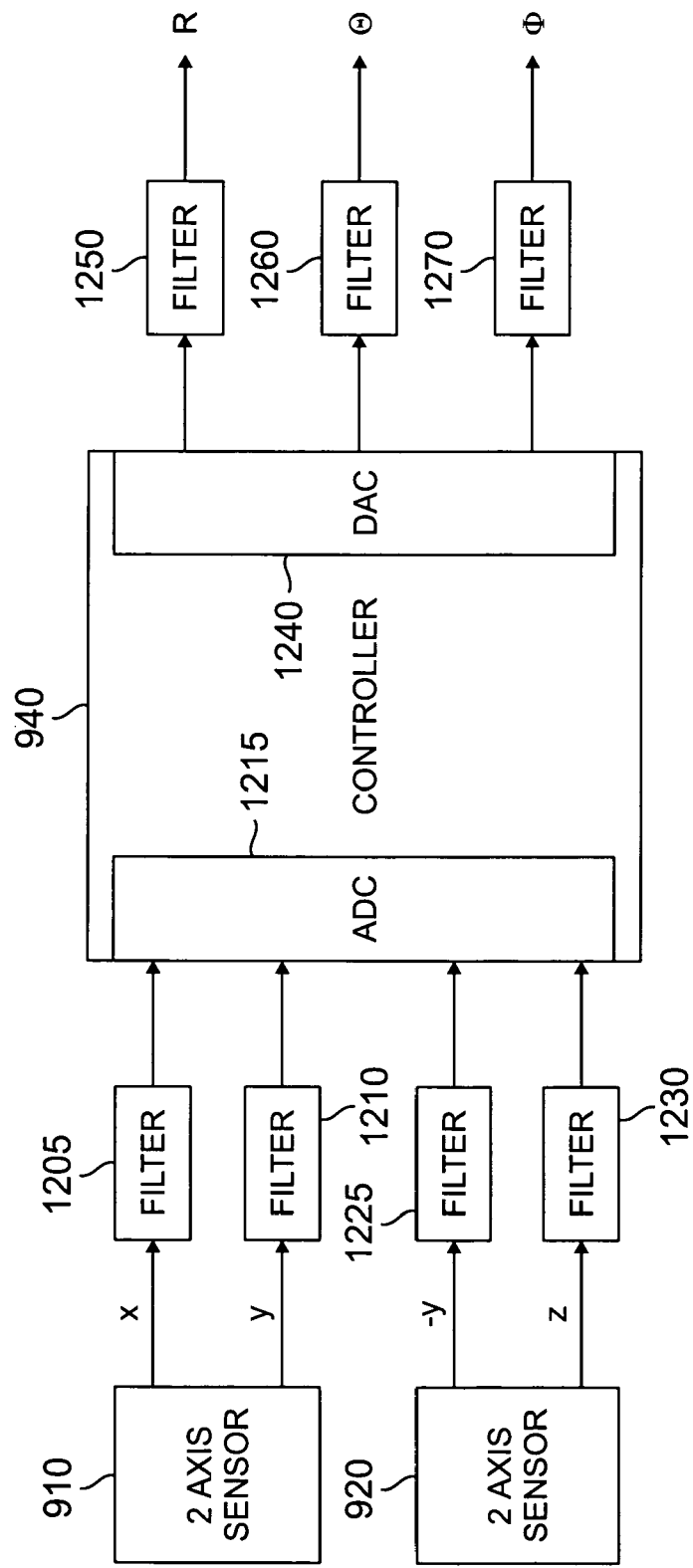
FIG. 12 illustrates an exemplary embodiment of the system of the present invention for evaluating body movement comprising two plural axis accelerometer sensors coupled to a controller.

FIG. 12 illustrates an exemplary embodiment of the present invention in which accelerometer 910 and accelerometer 920 are coupled to controller 940. Accelerometer 910 measures accelerations of the body in the positive x direction and in the positive y direction. Accelerometer 920 measures accelerations of the body in the negative y direction and in the positive z direction.

The analog x signal from accelerometer 910 is coupled to an analog digital converter (ADC) 1215 through filter 1205. Similarly, the analog y signal from accelerometer 910 is coupled to ADC 1215 through filter 1210. Filter 1205 and filter 1210 filter out noise artifacts and cancel high frequency elements that may cause analog to digital aliasing. Filter 1205 and filter 1210 may be partially implemented using digital signal processing within controller 940.

ADC 1215 converts analog signals from filter 1205 and filter 1210 to digital signals. ADC 1215 may be external to controller 940 or may be incorporated within controller 940.

Similarly, the analog −y (i.e., negative y) signal from accelerometer 920 is coupled to ADC 1215 through filter 1225. The analog z signal from accelerometer 920 is coupled to ADC 1215 through filter 1230. Filter 1225 and filter 1230 also filter out noise artifacts and cancel high frequency elements that may cause analog to digital aliasing. Filter 1225 and filter 1230 may be partially implemented using digital signal processing within controller 940.

Controller 940 uses the x, y, z acceleration values to calculate values for the x, y, z distances. This calculation is done by first calculating a time integral of the x, y, z acceleration values to obtain x, y, z velocity values. Then a time integral of the x, y, z velocity values is calculated to obtain the x, y, z distance values. Controller 940 then uses Equations (4), (5), and (6) to calculate the spherical polar (SP) coordinates R, $\Theta$, $\Phi$. Controller 940 then sends the digital form of the R, $\Theta$, $\Phi$ coordinates to digital to analog converter (DAC) 1240. DAC 1240 converts the digital form of the R, $\Theta$, $\Phi$ coordinates into an analog form. DAC 1240 may be external to controller 940 or may be incorporated within controller 940.

The analog R signal is filtered in filter 1250. The analog $\Theta$ signal is filtered in filter 1260. The analog $\Phi$ signal is filtered in filter 1270. The filtered R, $\Theta$, $\Phi$ signals are the spherical polar (SP) components of a vector that represents a measurement of the location of the body to which accelerometer 910 and accelerometer 920 are attached.

In one advantageous embodiment of the present invention, controller 940 uses indicating means 41 to transmit the SP coordinates to RF receiver 115 and processor 117 (as shown in FIG. 7). As previously mentioned, RF receiver 115 is tuned to receive transmissions from indicating means 41. As will be more fully described, processor 117 is capable of analyzing the SP coordinate information that it receives from controller 940.

As time passes, the body to which accelerometer 910 and accelerometer 920 and controller 940 are attached moves (or does not move). Therefore, controller 940 continually sends to processor 117 a stream of SP coordinates that represent the motion of the body. Memory 121 attached to processor 117 contains a library of prerecorded sets of SP coordinates in which each prerecorded set of SP coordinates represents a type of motion.

For example, a first prerecorded set of SP coordinates could represent inactivity or the absence of motion (i.e., "no motion"). The absence of motion could signify the existence of a problem condition. If the body to which accelerometer 910 and accelerometer 920 and controller 940 is attached is a person, then a "no motion" signal could mean that (1) the person has become unconscious and has ceased moving, or that (2) the sensor device has become detached from the person, or that (3) the sensor device has ceased to function properly.

A second prerecorded set of SP coordinates could represent a successful attempt to change position. A third prerecorded set of SP coordinates could represent an unsuccessful attempt to change position.

A fourth prerecorded set of SP coordinates could represent the motion of a body moving with a particular type of gait, and especially a gait that is associated with a disability (e.g., limping). The term "moving" generally refers to all types of motion such as walking, running, skipping, jogging, jumping, and other types of motion.

A fifth prerecorded set of SP coordinates could represent the motion of a person who is unsteady and is swaying back and forth.

A sixth prerecorded set of SP coordinates could represent the motion of a person who experiences a "near fall." A near fall occurs when a person loses his or her balance but recovers in time to keep from actually falling. A seventh prerecorded set of SP coordinates could represent the motion of a person who experiences an actual fall.

A series of different types of motion may be recorded in which each type of motion is represented by a prerecorded set of SP coordinates.

Processor 117 analyzes the SP coordinate information that it receives from controller 940 by comparing it with each prerecorded set of SP coordinates stored in memory 121. When processor 117 identifies a match between the measured set of SP coordinates from controller 940 and one of the prerecorded sets of SP coordinates stored in memory 121, then processor 117 generates and sends a message that a match has been found.

The message may be sent by audible alarm 123, LED bank 107 and/or retransmission unit 125. In this manner, controller 940 identifies types of motions that the body experiences including, without limitation, falls, near falls and particular types of gaits of motion.

The ability of processor 117 to detect patterns of motion that typically precede a fall is very useful in preventing falls. For example, an elderly or infirm person who attempts to rise from a bed or chair may be subject to falling. Assume that processor 117 detects a pattern of motion that typically occurs before a fall when a person is attempting to rise from a bed or a chair. Processor 117 can then activate an alarm to alert the person that a fall may be imminent. Upon hearing the alarm, the person is warned to cease his or her attempt to rise. A nearby caregiver may also hear the alarm and come to assist the person before a fall occurs. In this manner serious falls can be prevented.

In an alternate advantageous embodiment of the present invention, controller 940 contains the library of prerecorded sets of SP coordinates. In this embodiment, controller 940 performs the analysis of the SP coordinate data. When a match is found, controller 940 generates and sends a message (using indicating means 41) that a match has been found. An alarm may then be sounded in the manner previously described.

Figure 13:
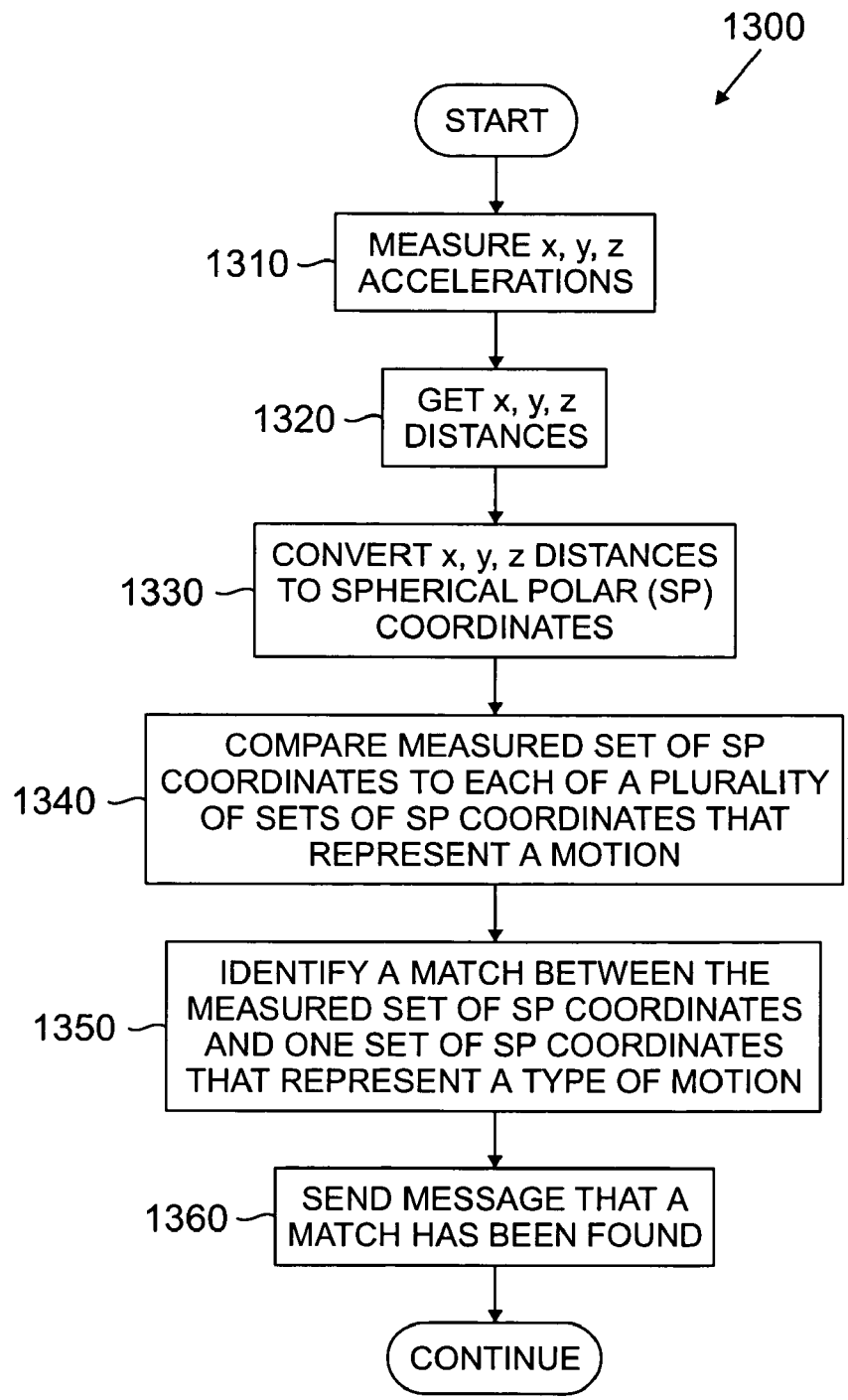
FIG. 13 illustrates a flow diagram showing a first portion of an advantageous embodiment of the method of the present invention.

FIG. 13 illustrates a flow diagram showing a first portion of an advantageous embodiment of the method of the present invention. The steps of the first portion of the method are collectively referred to with the reference numeral 1300. At the start of the method, accelerometer 910 and accelerometer 920 measure the x, y, z values of acceleration (step 1310). Controller 940 then calculates the x, y, z distance values (step 1320). Controller 940 then converts the x, y, z distance values to spherical polar (SP) coordinates (step 1330).

Processor 117 (or controller 940 in an alternative embodiment) compares a measured set of SP coordinates with each of the plurality of prerecorded sets of SP coordinates that represents a type of motion (step 1340). Processor 117 (or controller 940 in an alternative embodiment) identifies a match between the measured set of SP coordinates and one particular prerecorded set of SP coordinates that represents a type of motion (step 1350). Processor 117 (or controller 940 in an alternative embodiment) then sends a message that a match has been found (step 1360).

Figure 14:
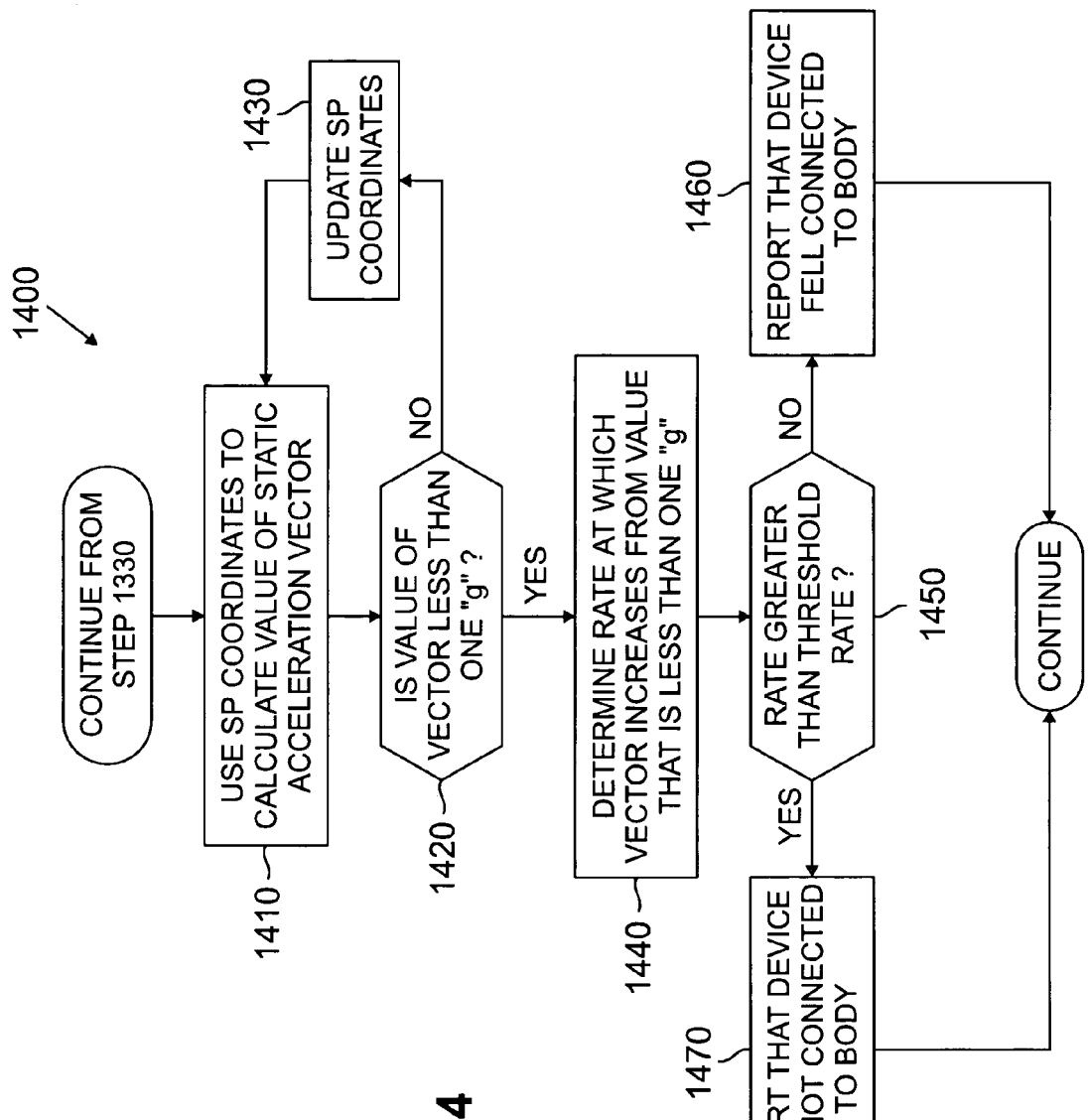
FIG. 14 illustrates a flow diagram showing a second portion of an advantageous embodiment of the method of the present invention.

FIG. 14 illustrates a flow diagram showing a second portion of an advantageous embodiment of the method of the present invention. The steps of the second portion of the method are collectively referred to with the reference numeral 1400.

The second portion of the method uses the SP coordinate data to calculate a value for a static acceleration vector that represents the value of the earth's gravitational acceleration. When an object falls in a vacuum (i.e., an environment where there is no frictional force due to air resistance) the sum of the components for the static acceleration vector is zero.

When a person loses his or her balance and falls, the measurement of the static acceleration vector that controller 940 records is not zero. The measured value is less than one "g" but is greater than a zero value. The value is greater than zero because the person's muscle tone (due to the slight contraction of skeletal muscles that is always present) operates to slow the person's body a little bit as the body falls. In some cases, objects may impede the person's fall or the person may reflexively grasp some object to slow the rate of fall.

When the value of the static acceleration vector reaches a value that is less than one "g" but greater than a zero value, that is an indication that controller 940 has experienced a fall. Unlike some types of prior art methods (e.g., tilt switches), this method of detecting a fall does not rely on detecting a change in the angle of orientation of the body. The occurrence of a fall is detected by detecting a reduction in the value of the static acceleration vector to a value that is less than one "g."

If controller 940 was not connected to a person's body during the fall, then the value of the static acceleration vector measured by controller 940 after the fall will instantaneously be equal to one "g." If controller 940 was connected to a person's body during the fall, then the value of the static acceleration vector measured by controller 940 after the fall will, rise relatively slowly. This is due to the fact that the person's muscle tone (due to the slight contraction of skeletal muscles that is always present) operates to slow the rise of the value of the static acceleration vector after the fall.

If the value of the static acceleration vector rises at a rate that is greater than a preselected threshold rate, then it is clear that controller 940 was not connected to a person's body during the fall. If the value of the static acceleration vector rises at a rate that is less than a predetermined threshold rate, then it is clear that controller 940 was connected to a person's body during the fall.

At the start of the second portion of the method of the present invention, controller 940 has converted the x, y, z distance values to spherical polar (SP) coordinates (step 1330). Controller 940 then uses the SP coordinates to calculate the value of the static acceleration vector (step 1410). Controller 940 determines whether the value of the static acceleration vector has reached a value that is less than one "g" (decision step 1420). If not, then controller 940 updates the SP coordinates (step 1430) and control returns to step 1410.

If the value of the static acceleration vector has reached a value that is less than one "g," then controller 940 determines the rate at which the value of the static acceleration vector is increasing from the value that is less than one "g" (step 1440). Processor 940 then compares the rate to a preselected threshold rate (decision step 1450). If the rate is greater than the preselected threshold rate, then controller 940 sends a message that controller 940 was not connected to the person's body during the fall (step 1470). If the rate is not greater than the preselected threshold rate, then controller 940 sends a message that controller 940 was connected to the person's body during the fall (step 1460). In this manner controller 940 is able to distinguish between a fall of controller 940 alone and a fall of controller 940 while controller 940 was coupled to a person's body.

Relatively rare instances may occur in which controller 940 will require additional information to distinguish between a fall of controller 940 alone and a fall of controller 940 while controller 940 is coupled to a person's body. As previously described, the measured value of acceleration of a falling person is usually less than one "g" but is greater than a zero value. The value is greater than zero because the person's muscle tone (due to the slight contraction of skeletal muscles that is always present) operates to slow the person's body a little bit as the body falls. This is true for normal falling situations.

However, it is not true in the relatively rare cases in which the falling person's body is not in contact with any object. For example, if a person falls off a ladder, then the person's body falls through the atmosphere and does not make contact with any object until impact with the floor or ground. In this type of fall the falling person's muscle tone does not operate to slow the person's body during the fall because the person is not in contact with an external object.

An alternate advantageous embodiment of the present invention can detect this type of fall. In the alternate embodiment controller 940 detects an additional signal to determine whether controller 940 was coupled to the falling person's body. For example, as previously described, controller 940 comprises processing circuitry 39 that is capable of receiving a signal from respiration module 73. Respiration module 73 is capable of detecting the respiration rate of the falling person.

In an alternate embodiment of the present invention, controller 940 detects a rate at which the value of the static acceleration vector is increasing from a value that is less than one "g". If the detected rate is greater than a preselected threshold rate (usually indicative of a fall of controller 940 not coupled to a body), then controller 940 determines whether a respiration signal was detected within a predetermined time period (e.g., six (6) seconds). If a respiration signal was detected, then processor 940 reports that the fall was a fall of controller 940 connected to a body and not a fall of controller 940 alone.

Although the present invention has been described in detail, those skilled in the art should understand that they can make various changes, substitutions and alterations herein without departing from the spirit and scope of the invention in its broadest form.

What is claimed is:

1. A system that evaluates movement of a body relative to an environment, said system comprising:
    a sensor, associable with said body, that senses accelerative phenomena of said body relative to a three dimensional frame of reference in said environment, said sensor comprising a plurality of acceleration measuring devices;
    a processor, associated with said sensor, that processes said sensed accelerative phenomena of said body as a function of at least one accelerative event characteristic to thereby determine whether said evaluated body movement is within an environmental tolerance, and to thereby determine whether said body has experienced acceleration that represents one of a plurality of different types of motion; and
    a controller containing said processor, said controller capable of receiving from said plurality of acceleration measuring devices a plurality of values of acceleration of body motion.

2. The system as set forth in claim 1 wherein one of said plurality of different types of motion is one of: no motion, a successful attempt to change position, an unsuccessful attempt to change position, a motion of a body moving with a gait, a motion of a body moving with a gait associated with a disability, a swaying motion, a near fall, and a fall.

3. The system as set forth in claim 1 wherein said controller is capable of using values of acceleration of body motion measured in a plurality of directions to calculate a plurality of values of distance components of said body motion in said plurality of directions.

4. The system as set forth in claim 3 wherein said controller is capable of comparing a set of coordinate components that represents a measurement of said body motion to each of a plurality of prerecorded sets of coordinate components in which each set of said plurality of sets of coordinate components represents a type of motion.

5. The system as set forth in claim 4 wherein one of said plurality of prerecorded sets of coordinate components represents one of: no motion, a successful attempt to change position, an unsuccessful attempt to change position, a motion of a body moving with a gait, a motion of a body moving with a gait associated with a disability, a swaying motion, a near fall, and a fall.

6. The system as set forth in claim 5 wherein said controller is capable of identifying a match between a set of coordinate components that represents a measurement of said body motion with one of a plurality of said prerecorded sets of coordinate components to identify a type of motion that corresponds to said body motion.

7. The system as set forth in claim 6 wherein after identifying said type of motion said controller sends an alarm signal indicative of said type of motion.

8. The system as set forth in claim 4 wherein said set of coordinate components comprises one of: a set of x, y, z coordinate components and a set of spherical polar coordinate components.

9. The system as set forth in claim 3 wherein said controller is capable of calculating a value of a static acceleration vector from said plurality of values of distance components of said body motion.

10. The system as set forth in claim 9 wherein said controller is capable of determining when said value of said static acceleration vector reaches a value less than the acceleration of gravity indicative of a fall; and wherein said controller is capable of determining a rate at which said value of said static acceleration vector increases after the value of said static acceleration vector has reached a value less than the acceleration of gravity indicative of a fall; and wherein said controller is capable of using said rate of increase of said value of said static acceleration vector to determine whether said controller was connected to a body during a fall that caused the value of said static acceleration vector to reach a value less than the acceleration of gravity.

11. A method of operating a system to evaluate movement of a body relative to an environment, said method of operation comprising the steps of:
    sensing, with a sensor associated with said body, accelerative phenomena of said body relative to a three dimensional frame of reference in said environment, wherein said sensor comprises a plurality of acceleration measuring devices;

processing, with a processor associated with said sensor, repeatedly sensed dynamic and static accelerative phenomena of said body as a function of at least one accelerative event characteristic to thereby determine whether said evaluated body movement is within an environmental tolerance;

determining whether said body has experienced acceleration that represents one of a plurality of different types of motion; and receiving in a controller containing said processor a plurality of values of acceleration of body motion from said plurality of acceleration measuring devices of said sensor.

12. The method as set forth in claim 11 wherein one of said plurality of different types of motion is one of: no motion, a successful attempt to change position, an unsuccessful attempt to change position, a motion of a body moving with a gait, a motion of a body moving with a gait associated with a disability, a swaying motion, a near fall, and a fall.

13. The method as set forth in claim 11 further comprising the step of:

calculating in said controller a plurality of values of distance components of said body motion from said values of acceleration of body motion measured in a plurality of directions.

14. The method as set forth in claim 13 further comprising the step of:

comparing in said controller a set of coordinate components that represents a measurement of said body motion to each of a plurality of prerecorded sets of coordinate components in which each set of said plurality of sets of coordinate components represents a type of motion.

15. The method as set forth in claim 14 wherein one of said plurality of prerecorded sets of coordinate components represents one of: no motion, a successful attempt to change position, an unsuccessful attempt to change position, a motion of a body moving with a gait, a motion of a body moving with a gait associated with a disability, a swaying motion, a near fall, and a fall.

16. The method as set forth in claim 15 further comprising the steps of:

identifying in said controller a match between a set of coordinate components that represents a measurement of said body motion with one of a plurality of said prerecorded sets of coordinate components; and identifying a type of motion that corresponds to said body motion.

17. The method as set forth in claim 16 further comprising the step of:

sending an alarm signal from said controller indicative of said type of motion after said type of motion has been identified.

18. The method as set forth in claim 14 wherein said set of coordinate components comprises one of: a set of x, y, z coordinate components and a set of spherical polar coordinate components.

19. The method as set forth in claim 13 further comprising the step of:

calculating in said controller a value of a static acceleration vector from said plurality of values of distance components of said body motion.

20. The method as set forth in claim 19 further comprising the steps of:

determining in said controller when said value of said static acceleration vector reaches a value less than the acceleration of gravity indicative of a fall;

determining in said controller a rate at which said value of said static acceleration vector increases after the value of said static acceleration vector has reached a value less than the acceleration of gravity indicative of a fall; and using said rate of increase of said value of said static acceleration vector to determine in said controller whether said controller was connected to a body during a fall that caused the value of said static acceleration vector to reach a value less than the acceleration of gravity.

* * * * *

UNITED STATES PATENT AND TRADEMARK OFFICE
CERTIFICATE OF CORRECTION

PATENT NO. : 7,095,331 B2  Page 1 of 1
APPLICATION NO. : 10/796595
DATED : August 22, 2006
INVENTOR(S) : Michael L. Lehrman, Michael D. Halleck and Edward L. Massman It is certified that error appears in the above-identified patent and that said Letters Patent is hereby corrected as shown below:

On the Title page of the patent at (75) Inventors: after "Edward L. Massman, Dallas, TX (US)" please insert -- ; Michael E. Halleck and Alan R. Owens, both of Longmont, CO (US) --

Signed and Sealed this
Third Day of March, 2015

Michelle K. Lee
*Deputy Director of the United States Patent and Trademark Office*

Disclaimer

7,095,331 B2 - Michael L. Lehrman, Washington, DC (US); Michael D. Halleck, Northglenn, CO (US); Edward L. Massman, Dallas, TX (US). SYSTEM AND METHOD FOR DETECTING MOTION OF A BODY. Patent dated August 22, 2006. Disclaimer filed June 30, 2016, by the assignee, iLife Technologies, Inc.

I hereby disclaim the following complete Claims 1-2 and 11-12 of said patent.

*(Official Gazette, January 6, 2026)*

(12) INTER PARTES REVIEW CERTIFICATE (510th)
United States Patent     (10) Number:    US 7,095,331 K1
Lehrman et al.     (45) Certificate Issued:    Feb. 9, 2018

(54) SYSTEM AND METHOD FOR DETECTING MOTION OF A BODY

(75) Inventors: Michael L. Lehrman; Michael D. Halleck; Edward L. Massman

(73) Assignee: ILIFE TECHNOLOGIES, INC.

Trial Number:

IPR2015-00112 filed Oct. 21, 2014

Inter Partes Review Certificate for:

Patent No.: 7,095,331
Issued: Aug. 22, 2006
Appl. No.: 10/796,595
Filed: Mar. 9, 2004

The results of IPR2015-00112 are reflected in this inter partes review certificate under 35 U.S.C. 318(b).

INTER PARTES REVIEW CERTIFICATE
U.S. Patent 7,095,331 K1
Trial No. IPR2015-00112
Certificate Issued Feb. 9, 2018

AS A RESULT OF THE INTER PARTES REVIEW PROCEEDING, IT HAS BEEN DETERMINED THAT:

Claims 1, 2, 11 and 12 are cancelled.

* * * * *